(12) United States Patent
Li et al.

(10) Patent No.: US 7,238,496 B2
(45) Date of Patent: Jul. 3, 2007

(54) RAPID AND AUTOMATED ELECTROCHEMICAL METHOD FOR DETECTION OF VIABLE MICROBIAL PATHOGENS

(75) Inventors: Yanbin Li, Fayetteville, AR (US); Liju Yang, Fayetteville, AR (US); Chuanmin Ruan, State College, PA (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 347 days.

(21) Appl. No.: 10/635,164

(22) Filed: Aug. 6, 2003

(65) Prior Publication Data

US 2004/0175780 A1     Sep. 9, 2004

Related U.S. Application Data

(60) Provisional application No. 60/401,489, filed on Aug. 6, 2002.

(51) Int. Cl.
*C12Q 1/04* (2006.01)
(52) U.S. Cl. ...................................... 435/34
(58) Field of Classification Search ................ 435/34, 435/29, 7.32, 7.35, 7.37, 252.1, 817, 4
See application file for complete search history.

(56) References Cited

U.S. PATENT DOCUMENTS

| | | | |
|---|---|---|---|
| 4,115,230 A | 9/1978 | Beckman | |
| 4,321,322 A | 3/1982 | Ahnell | |
| 4,517,291 A | 5/1985 | Seago | |
| 5,098,547 A | 3/1992 | Bryan et al. | |
| 5,126,034 A | 6/1992 | Carter et al. | |
| 5,348,862 A | 9/1994 | Pasero et al. | |
| 5,660,998 A | 8/1997 | Naumann et al. | |
| 6,068,748 A | 5/2000 | Berger et al. | |
| 6,203,996 B1 | 3/2001 | Duffy et al. | |
| 2001/0053535 A1* | 12/2001 | Bashir et al. ................ | 435/34 |

OTHER PUBLICATIONS

Hara-Kudo et al, Applied and Env. Microb., pp. 2866-2872, V. 66, (Jul. 2000).*
Sharma et al, Applied Microbio., v. 18, No. 4, pp. 589-595, (1969).*
Budu-Amoako et al , Applied and Envir. Micro, v. 58, No. 9, pp. 3177-3179, (Sep. 1992).*
Comprehensive Reviews in Food Sci. and Food Safety, vol. 1, pp. 17-22, (2002).*
ANONYMOUS, Update: Multistate Outbreak of Listeriosis—United States, 1998-1999, Morbidity and Mortality Weekly Report 47, 1117-1118, U.S. Department of Health & Human Services, Jan. 8, 1999.
ANONYMOUS, Multistate Outbreak of Listeriosis—United States, 2000, Morbidity and Mortality Weekly Report 49, 1129-1130, U.S. Department of Health & Human Services, Dec. 22, 2000.
Crowley, E., et al., Increasing the sensitivity of *Listeria monocytogenes* assays: evaluation using ELISA and amperometric detection, Analyst, 124, 295-299, 1999.
Chen, W., et al., Molecular Beacons: A Real-Time Polymerase Chain Reaction Assay for Detecting *Salmonella*, Analytical Biochemistry, 280, 166-172, 2000.
Curiale, M., et al., Enzyme-Linked Immunoassay for Detection of *Listeria monocytogenes* in Dairy Products, Seafoods, and Meats: Collaborative Study, Journal of AOAC international, 77, 1472-1489, 1994.
Dickertmann, D., et al., Electrochemical Formation and Reduction of Monomolecular Oxide Layers in (111) and (100) Planes of Gold Single Crystals, Electroanalytical Chemistry and Interfacial Electrochemistry, 55, 429-443, 1974.
Duffy, G., et al., A comparison of immunomagnetic and surface tension adhesion immunofluorescent techniques for the rapid detection of *Listeria monocytogenes* and *Listeria innocua* in meat, Letters in Applied Microbiology, 24, 445-450, 1997.
Firstenberg-Eden, R., et al., A new rapid automated method for the detection of *Listeria* from environmental swabs and sponges, International Journal of Food Microbiology, 56, 231-237, 2000.
Karunasagar, I., et al., *Listeria* in tropical fish and fishery products, International Journal of Food Microbiology, 62, 177-181, 2000.
Kerdahi, K., et al., Comparative Study of Colorimetric and Fully Automated Enzyme-Linked Immunoassay System for Rapid Screening of *Listeria* spp. in Foods, Journal of AOAC International, 80, 1139-1142, 1997.
Mattingly, J., et al., Rapid Monoclonal Antibody-Based Enzyme-Linked Immunosorbent Assay for Detection of *Listeria* in Food Products, J. Assoc. Off. Anal. Chem., 71, 679-681, 1988.
McKillip, J., et al., A comparison of methods for the detection of *Escherichia coli* O157:H7 from artifically contaminated dairy products using PCR, Journal of Applied Microbiology, 89, 49-55, 2000.
Norton, D., et al., Application of BAX for Screening/Genus *Listeria* Polymerase Chain Reaction System for Monitoring *Listeria* Species In Cold-Smoked Fish and in the Smoked Fish Processing Environment, Journal of Food Protection, 63, 343-346, 2000.

(Continued)

*Primary Examiner*—Jon Weber
*Assistant Examiner*—Kailash C. Srivastava
(74) *Attorney, Agent, or Firm*—Jill A. Fahrlander; Michael Best & Friedrich LLP (57) ABSTRACT

A method for in situ detection of viable pathogenic bacteria in a selective medium by measuring cathodic peak current of oxygen on cyclic voltammograms during bacterial proliferation with an electrochemical voltammetric analyzer. The rapid oxygen consumption at a time during the growth of bacteria resulted in a sharp decline of the cathodic peak current curves. The detection times (threshold values) obtained from the cathodic peak current curve were inversely related to the concentrations of the pathogenic bacteria in the medium. This method for detection of pathogenic bacteria is more sensitive than nucleic acid-based polymerase chain reaction (PCR) methods and any of antibody-based methods such as enzyme-linked immunosorbent assay (ELISA) technology, electrochemical immunoassays, immunosensors, and it has a sensitivity similar to conventional culture methods and impedimetric methods but is more rapid than both of them. A calibration curve was obtained by plotting initial cell concentrations (CFU/ml) determined by conventional plate counting, as a function of the detection time.

9 Claims, 11 Drawing Sheets

OTHER PUBLICATIONS

Powell, H., Proteinase Inhibition of the detection of *Listeria monocytogenes* in milk using the polymerase chain reaction, Letters in Applied Microbiology, 18, 59-61, 1994.

Scheu, P., et al., Detection of pathogenic and spoilage microorganisms in Food with the polymerase chain reaction, Food Microbiology, 15, 13-31, 1998.

Scheu, P., et al., Rapid detection of *Listeria monocytogenes* by PCR-ELISA, Letters in Applied Microbiology, 29, 416-420, 1999.

Shaw, S., et al., Performance of the Dynabeads Anti-*Salmonella* System in the Detection of *Salmonella* Species in Foods, Animal Feeds, and Environmental Samples, Journal of Food Protection, 61, 1507-1510, 1998.

Silley, P., et al., Impedance microbiology—a rapid change for microbiologists, Journal of Applied Bacteriology, 80, 233-243, 1996.

Stewart, D., et al., Specificity of the BAX Polymerase Chain Reaction System for Detection of the Foodborne Pathogen *Listeria monocytogenes,* Journal of AOAC International, 81, 817-822, 1998.

Wawerla, M., et al., Impedance Microbiology: Applications in Food Hygiene, Journal of Food Protection, 62, 1488-1496, 1999.

Che, Y., et al., Rapid Detection of *Salmonella typhimurium* Using an Immunoelectrochemical Method Coupled with Immunomagnetic Separation, Journal of Rapid Methods and Automation in Microbiology, 7, 47-59, 1999.

Ogden, I., et al., A modified conductance medium for the detection of *Salmonella* spp., Journal of Applied Bacteriology, 63, 459-464, 1987.

Gibson, D., et al., Automated Conductance Method for the Detection of *Salmonella* in Foods: Collaborative Study, Journal of AOAC International, 75, 293-302, 1992.

Gibson, D., et al., Some modification to the media for rapid automated detection of *Salmonellas* by conductance measurement, Journal of Applied Bacteriology, 63, 299-304, 1987.

Felice, C., et al., Impedance microbiology: quantification of bacterial content in milk by means of capacitance growty curves, Journal of Microbiological Methods, 35, 37-42, 1999.

Wang, X., et al., Rapid Detection of *Salmonella* in Chicken Washes by Immunomagetic Separation and Flow Cytometry, Journal of Food Protection, 62, 717-723, 1999.

Swaminathan, B., et al., Rapid Detection of Food-Borne Pathogenic Bacteria, Annual Review of Microbiology, 48, 401-426, 1994.

Koubova, V., et al., Detection of foodborne pathogens using surface plasmon resonance biosensors, Sensors and Actuators, B 74, 100-105, 2001.

Brewster, J., et al., Immunoelectrochemical Assays for Bacteria: Use of Epifluorescence Microscopy and Rapid-Scan Electrochemical Techniques in Development of an Assay for *Salmonella,* Analytical Chemistry, 68 4153-4159, 1996.

Che, Y., et al., Rapid Detection of *Salmonella typhimurium* in Chicken Carcass Wash Water Using an Immunoelectrochemical Method, Journal of Food Protection, 63, 1043-1048, 2000.

Cloak, O., et al., Development of an Surface Adhesion Immunofluorescent Technique for the rapid detection of *Salmonella* spp. from meat and poultry, Journal of Applied Microbiology, 86, 583-590, 1999.

Cudjoe, K., et al., Immunomagnetic separation of *Salmonella* from foods and their detection using immunomagnetic particle (IMP)-ELISA, International Journal of Food Microbiology, 27, 11-25-1995.

Gehring, A., et al., Enzyme-linked immunomagnetic electrochemical detection of *Salmonella typhimurium,* Journal of Immunological Methods, 195, 15-25, 1996.

Ivnitski, D., et al., Biosensors for detection of pathogenic bacteria, Biosensors & Bioelectronics, 14, 599-624, 1999.

Park, I., et al., Thiolated *Salmonella* antibody immobilization onto the gold surface of piezoelectric quartz crystal, Biosensors & Bioelectronics, 13, 1091-1097, 1998.

Mansfield, L., et al., The detection of *Salmonella* using a combined immunomagnetic separtaion and ELISA end-detection procedure, Letters in Applied Microbiology, 31, 279-283, 2000.

Mead, P., et al., Food-Related Illness and Death in the United States, Emerging Infectious Diseases, 5, 607-625, Sep.-Oct. 1999.

Tian, H., et al., Rapid Detection of *Salmonella* spp. in Foods by Combination of a new Selective Enrichment and a Sandwich ELISA Using two Monoclonal Antibodies against Dulcitol 1-Phosphate Dehydrogenase, Journal of Food Protection, 59, 1158-1163, 1996.

Van Der Zee, H., et al., Rapid and Alternative Screening Methods for Microbiological Analysis, Journal of AOAC International, 80, 934-940, 1997.

Ruan, C., et al., Rapid detection of viable *Salmonella typhimurium* in a selective medium by monitoring oxygen consumption with electrochemical cyclic voltametry, Journal of Electroanalytical Chemistry, 519, 33-38, Feb. 8, 2002 (available online Dec. 11, 2001).

Ruan, C., et al., Detection of Viable *Listeria monocytogenes* in Milk Using an Electrochemical Method, Journal of Rapid Methods and Automation in Microbiology, 11, 11-22, 2003.

Matsunaga, T., et al., Electrode System for the Determination of Microbioal Populations, Applied and Environmental Microbiology, 37, 117-121, Jan. 1979.

Jay, J., Foodborn Gastroenteritis Caused by *Salmonella* and *Shigella, in Modern Food Microbiology,* $5^{th}$ Ed. Chapman & Hall, New York, 511-530, 1996.

Andrews, W., et al., Chap. 5, *Salmonella,* in FDA Bacteriological Analytical Manual, $8^{th}$ Edition, AOAC International, pp. 5.01-5.20, 1995.

Batt, C., Chap. 8, Rapid Methods for Detection of *Listeria,* in *Listeria, Listeriosis* and Food Safety, $2^{nd}$ Edition, Marcel Dekker, New York, pp. 261-278, 1999.

Ruan, C., et al., Poster, Rapid Detection of Viable *Salmonella* typhimurium in a Selective Medium by Monitoring Oxygen Consumption with Electrochemical Cyclic Voltammetry, presented at Food Safety Consortium 2001 Annual Meeting, Ames, Iowa, Sep. 16-18, 2001, 1 page.

Ruan, C., et al., Abstract, Rapid Detection of Viable *Salmonella* typhimurium in a Selective Medium by Monitoring Oxygen Consumption with Electrochemical Cyclic Voltammetry, in Food Safety Consortium 2001 Annual Meeting-Agenda, Presentations, and Progress Reports, Food Safety Consortium 2001 Annual Meeting, Ames, Iowa, p. AB-15, Sep. 16-18, 2001.

Wilkins, J., Use of Platinum Electrodes for the Electrochemical Detection of Bacteria, Applied and Environmental Microbiology, 36(5): 683-687, Nov. 1978.

* cited by examiner

RAPID AND AUTOMATED ELECTROCHEMICAL METHOD FOR DETECTION OF VIABLE MICROBIAL PATHOGENS

CROSS-REFERENCE TO RELATED APPLICATIONS

The present application claims the benefit of U.S. Provisional Application No. 60/401,489 filed Aug. 6, 2002, which is incorporated herein by reference.

STATEMENT REGARDING FEDERALLY SPONSORED RESEARCH OR DEVELOPMENT

The invention was made with Government support under the terms of Grant No. 99-34211-7563 awarded by USDA/CSREES. The Government has certain rights in the invention.

BACKGROUND OF THE INVENTION

1. Field of the Invention

This invention pertains to a method for the detection of viable pathogenic bacteria in a food or water sample.

2. Brief Description of the Related Art

Various pathogenic bacteria are known to be borne by food products, water or the like. These pathogenic bacteria can include *Salmonella typhimurium, Listeria monocytogenes, Escherichia coli* O157:H7 and the like. *Salmonella typhimurium* is considered to be one of the most virulent foodborne pathogens. The ingestion of these organisms via contaminated food or water may lead to salmonellosis, a serious bacterial toxi-infection-syndrome associated with gastroenteritis, typhoid and parathyphoid fevers (J. M. Jay, Foodborne gastroenteritis caused by *Salmonella* and *Shigella*. In: Modern food microbiology, 5th ed., Chapman & Hall: New York, 1996). Each year, an estimated 1.4 million human *Salmonella* infections occur in the United States, causing an estimated 80,000–160,000 persons to seek medical attention, and resulting in 16,000 hospitalizations and nearly 600 deaths (P. S. Mead, et al., Emerging Infect. Dis. 5 (1999) 607). Hence, detection and control of this and similar pathogens is extremely important for the safety of food products and our health. The conventional microbiological methods based on culture enrichment techniques and plating procedures are highly sensitive and selective for bacterial detection but are cumbersome and time-consuming, requiring 3–4 days for presumptive results and 5–7 days for confirmation (W. H. Andrews, et al., Food and Drug Administration Bacteriological Analytical Manual, 8th ed., AOAC International: 1995, 5.01–5.20). There is a pressing need for tests for viable pathogenic bacteria that provide results more rapidly with a sensitivity similar to, or even better than that of the conventional methods. These tests should be simple, reproducible and specific, minimizing false-positive results.

Recently, many rapid methods have been investigated to meet the need for detection of viable pathogenic bacteria in food, environmental and clinical samples. These may be broadly classified into growth methods in which cell growth is a requirement of the detection process, and non-growth methods in which no cell growth is required in the detection steps.

The antibody-based test for bacteria detection is a kind of non-growth method. Many types of immunological tests have been developed for detection of *Salmonella* and other pathogenic bacteria. These can be divided into those based on enzyme-linked immunosorbent assay (ELISA) (L. P. Mansfield, S. J. Forsythe, Lett. Appl. Microbiol. 31 (2000) 279; H. Van Der Zee, J. H. J. Huis In't Veld, J. AOAC international. 4 (1997) 934; K. S. Cudjoe, et al., Intl. J. Food Microbiol. 27 (1995) 11), fluorescent-antibody straining (immunofluorescent assays) (O. M. Cloak, et al., J. Appl. Microbiol. 86 (1999) 583), and various other antibody-based techniques such as immunoelectrochemical assays (J. D. Brewster, et al., Anal. Chem. 68 (1996) 4153; A. G. Gehring, et al., J. Immunol. Methods, 195 (1996) 15; Y. H. Che, et al., J. Food. Prot. 63 (2000) 1043), immunosensors (D. Ivnitski, et al., Biosens. Bioelectron. 14 (1999) 599; I. S. Park, N. Kim, Biosens. Bioelectron. 13 (1998) 1091; V. Koubova, et al., Sens. Actuators B. 74 (2001) 100), immunochromatographic methods (B. Swaminathan, Ann. Rev. Microbiol. 48 (1994) 401) and flow cytometry coupled with fluorescent antibodies (X. Wang, M. F. Slavik, J. Food Prot. 62 (1999) 717). These antibody-based methods reduce analysis time and give presumptive results in several hours to one day, when compared with culture plating procedures that require two to three days. The detection limit of these methods for *Salmonella* varies from $10^4$ to $10^6$ cells/ml. Since *Salmonella* cells in samples, especially, in food samples are usually present in small numbers, pre-enrichment is necessary to obtain the target cell concentration in detectable levels for applications of these methods. Furthermore, the detection sensitivity of these antibody-based methods is dominated by the quality of corresponding antibodies and labeled antibodies. Due to the low binding efficacy of *Salmonella* to its corresponding antibodies and the non-specific binding of antibodies, it is very difficult to further lower the detection limit for *Salmonella* using the antibody-based methods.

Nucleic acid-based assay for bacteria is another kind of non-growth method. The progress of a DNA amplification system called polymerase chain reaction (PCR) makes the assay much more sensitive for bacteria (W. Chen, G. Martinez, A. Mulchandani, Anal. Biochem. 280 (2000) 166). However, the PCR based assay is even more labor-intensive than ELISA and thus far more labor-intensive than modified conventional or automated methods (C. Wray, A. Wray, *Salmonella* in domestic animals, Oxford, N.Y., 2000). It also requires more than 4 hours to complete the test.

Impedance methods are based on the measuring the relative or absolute change in impedance, conductance and/or capacitance of a medium, as the result of metabolic activities of the microorganisms (P. Silley, S. Forsythe, J. Appl. Bacteriol. 80 (1996) 233; C. J. Felice, et al., J. Microbiol. Methods. 35 (1999) 37). Impedance enumeration of microorganisms relies on the detection time obtained from the impedance curve being inversely related to sample contamination (M. Wawerla, A. Stolle, B. Schalch, H. Eisgeruber, J. Food. Prot. 62 (1999) 1488). Impedance method has advantages over conventional microbiological methods. It reduces the analysis time to 15 h for the detection of *Salmonella* using selenite-cystine/trimethylamine oxide/mannitol (SCT/M) medium and had the same sensitivity as the conventional method (D. M. Gibson, J. Appl. Bacteriol. 63 (1987) 299). In fact, the impedance method is accepted by the Association of Official Analytical Chemists (AOAC) as a first action method (D. M. Gibson, P. Coombs, D. W. Pimbley, J. Assoc. Off. Anal. Chem. 75 (1992) 293).

SUMMARY OF INVENTION

A new method for in situ monitoring of viable pathogenic bacteria, such as *Salmonella typhimurium* or the like, in a selective medium was developed by measuring cathodic peak current of oxygen on cyclic voltammograms during bacterial proliferation with an electrochemical voltammetric analyzer. The rapid oxygen consumption at a time during the growth of bacteria resulted in a sharp decline of the curves. The detection times (threshold values) obtained from the oxygen consumption curve were inversely related to the concentrations of viable pathogenic bacteria in the medium. This method for detection of viable pathogenic bacteria is more sensitive than nucleic acid-based polymerase chain reaction (PCR) methods and any of antibody-based methods such as enzyme-linked immunosorbent assay (ELISA) technology, electrochemical immunoassays, immunosensors, and it has a sensitivity similar to conventional culture methods and impedimetric methods but is more rapid than either of them. A calibration curve was obtained by plotting initial cell concentrations (CFU/ml) determined by conventional plate counting, as a function of the detection time. In the case of S. typhimurium, a linear response was found on the calibration curve between $1~2\times10^0$ and $1~2\times10^6$ cells/ml. The detection time for $1~2\times10^0$ and $1~2\times10^6$ cells/ml of viable S. typhimurium in the medium was 10 and 2.1 h, respectively.

We report a novel approach for direct monitoring of pathogenic bacteria, such as S. typhimurium, Listeria monocytogenes, Escherichia coli O157:H7 or the like, in a selective medium. The principle of this method is based on recording the oxygen reduction peak on a gold electrode surface in a selective medium using electrochemical cyclic voltammetry. For example, the growth of S. typhimurium in selenite cystine medium supplemented with mannitol (SC/M) consumes oxygen dissolved in the medium. The oxygen peak current could decrease sharply at a time during the growth of bacteria. This time on the oxygen consumption curve was termed as the detection time (threshold value), and was inversely related to the concentrations of Salmonella typhimurium in the samples.

DETAILED DESCRIPTION OF THE INVENTION

Medium and Cyclic Voltammetry

The cyclic voltammetry method was explored for detection of live pathogenic bacteria in pure culture and food samples. The method opened a new way for rapid detection of pathogens based on the measurement of changes in electrochemical properties of a medium resulting from the growth of bacteria. It achieved the detection limit as low as 1–2 cells in the medium which is lower than those of most other rapid methods such as antibody-based methods ($10^3$–$10^6$ CFU/ml) and DNA-based methods ($10^1$–$10^4$ CFU/ml), and is similar to those of conventional methods. Importantly, it is much more rapid than conventional methods, and comparative to other rapid methods. Additionally, this method is readily to be automated and easy to operate.

The principle of this method is based on cyclic voltammetric measurement of oxygen consumption during the growth of bacteria. Cyclic voltammograms are recorded at regular time intervals during the growth of bacteria at a given temperature. The cathodic peak current of oxygen obtained from the cyclic voltammogram is plotted against the bacterial growth time, generating the oxygen consumption curve. The time corresponding to a point on the oxygen consumption curve at which time the decrease in the current exceeds a threshold value is defined at the detection time. The detection time is inversely proportional to the initial cell concentration in the medium. Enumeration of bacteria is accomplished using a calibration curve which is generated by plotting the initial cell concentration, which is determined by a surface plate method, as a function of the detection time.

A gold electrode was chosen as the working electrode to form the three electrode system including a platinum auxiliary electrode and an Ag|AgCl reference electrode. Only a gold electrode produced a good cycle voltammetric peak of oxygen; other electrodes, such as glassy carbon and platinum did not work.

The use of a selective medium is a key component to ensure selectivity of this method. The selective medium has to support the selective and rapid growth of the target bacteria.

Figure 5:
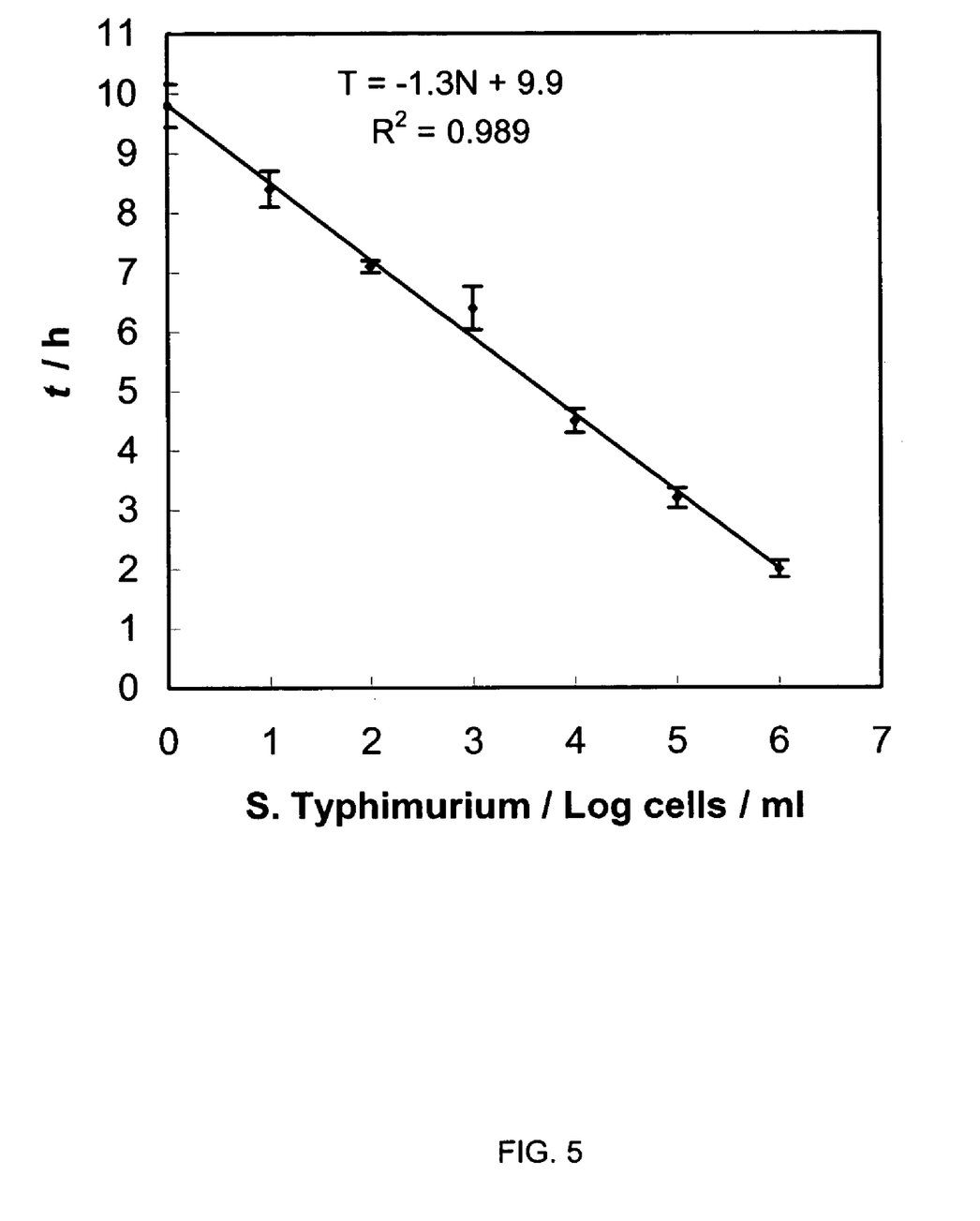
FIG. 5 is the calibration curve for detection of S. typhimurium using the cyclic voltammetry. Error bars represent the standard deviation of three replicates.

Selenite cystine (SC) has been used as an enrichment medium for the isolation of Salmonella from feces, urine or other pathological materials. Components of SC medium are casein enzymic hydrolysate, lactose, sodium hydrogen selenite, L-cystine and disodium phosphate. Casein enzymatic hydrolysate provides nitrogenous substances for microorganisms. Lactose maintains the pH of the medium as selenite is reduced by bacterial growth and alkali is produced. L-cystine improves the recovery of *S. typhimurium*. Mannitol was added into the medium as a carbon source for the growth of *Salmonella*. Selenite cystine trimethylamine-N-oxide/mannitol (SCT/M) medium is a common one for detection of *S. typhimurium* by impedance methods (D. M. Gibson, J. Appl. Bacteriol. 63 (1987) 299; I. D. Ogden, D. C. Cann, J. Appl. Bacteriol. 63 (1987) 459). The growth of bacteria produced trimethylamine-N-oxide (TMAO) reductase, which may reduce TMAO to charged trimethylamine (TMA) and result in changes in medium impedance.

*Salmonella typhimurium* was successfully detected using this method. Selenite-cystine broth supplemented with 5 g/l mannitol (SC/M) was used as a selective medium for the growth of *S. typhimurium*. Trimethylamine-N-oxide was not added into the medium because the impedance signal was not a measurement signal in quantifying microorganism using cyclic voltammetric method. The sodium hydrogen selenite in the SC broth is the component to ensure selective growth of *S. typhimurium*, and the addition of mannitol provides a sufficient carbon source for the rapid growth of the bacteria. The dissolved oxygen in this medium was reduced on the gold electrode at −0.35 V in cyclic voltammetric measurement. This cathodic peak current of oxygen was plotted as a function of the bacterial growth time, generating the oxygen consumption curve of *S. typhimurium*. The detection time ($t_d$) obtained from the oxygen curve had a linear relationship with the concentration of *S. typhimurium* (N) in the range of $10^0$ to $10^6$ CFU/ml. The regression equation was determined to be $t_d$=−1.33N+9.9 with $R^2$=0.989. Bacteria concentration at 1–2 CFU/ml and 1–2×$10^6$ CFU/ml was detected within 10 h and 2.1 h, respectively. The detection limit was 1–2 CFU/ml in the medium. The reproducibility was demonstrated as 3 replicates at each bacteria concentration were tested. The selectivity to *S. typhimurium* was verified as the competing pathogens, *E. coli* O157:H7 and *L. moncytogenes*, did not interfere the detection.

Cyclic voltammogram of Au electrode in the SC/M medium in FIG. 1 (curve a) shows that an anodic peak at +1.1 V (vs Ag|AgCl) during a forward scan from −0.6 to +1.2 V, a cathodic peak at +0.5 V (vs Ag|AgCl) and another cathodic peak at −0.35 V (vs Ag|AgCl) during a backward scan from +1.2 V to −0.6 V at a scanning rate of 100 mV/s. It has been reported that the oxide films of Au could be formed on the Au electrode surface during anodic scan in a water solution (D. Dickertmann, et al., J. Electroanal. Chem. 55 (1974) 429). The anodic peak of Au electrode in the SC/M medium at +1.1 V (vs Ag|AgCl) should be the formation of surface oxide, $Au+H_2O-e\rightarrow Au(OH)+H^+$, the cathodic peak at +0.5 V (vs Ag|AgCl) corresponds to cathodic dissolution of the surface oxide formed on the forward scan. The cathodic peak at −0.35 V (vs Ag|AgCl) corresponds to the reduction of oxygen dissolved in the medium. This can be proved by bubbling pure nitrogen and oxygen through the medium. FIG. 1 (curve b) indicated that the cathodic peak at −0.35 V (vs Ag|AgCl) disappeared after bubbling pure nitrogen for 5 min in the medium. The cathodic peak at −0.35 V (vs Ag|AgCl) appeared again after bubbling pure oxygen for 5 min in the deoxygenated medium. This cathodic peak corresponding to electro-reduction of dissolved oxygen at Au electrode in the medium is an indicator for the growth of microorganisms and the base for enumeration of microorganisms.

Effect of the Growth of *S. typhimurium* on Cyclic Voltammograms

The cyclic voltammograms of Au electrode in the SC/M medium containing 1~2 cell/ml of *S. typhimurium* was automatically recorded at every 10 min with a scan potential range from −0.6 v to 1.0 v (vs Ag|AgCl) at a scan rate of 100 mV/s. FIG. 2 shows the obtained cyclic voltammograms during the growth of *S. typhimurium*. The cathodic peak current corresponding to electro-reduction of dissolved oxygen on Au electrode surface at −0.35 v (vs Ag|AgCl) decreased with the growth of *S. typhimurium*, and this cathodic peak disappeared completely at about 10.5 h after adding *S. typhimurium* into the medium. The peak current deceased slowly during the first 9 h growth of *S. typhimurium* (from 3.83 μA to 3.0 μA) (FIG. 2 (curves a, b)), however, from 9 to 10.5 h, only a period of 1.5 h, the peak current decreased from 3.0 μA to 0.5 μA (FIG. 2 (curve c)). The growth cycle of microorganisms consists of four phases, and the beginning of the cycle is the 'lag phase'. Increases in cell numbers are not observed during this time. In the second phase, the cell number increases exponentially. In the stationary phase, neither the rate of growth nor the number cells continues increasing. The final phase of the cycle is the 'death phase' since the cell viability decreases. The growth cycle of microorganisms accounts for the change of the cyclic voltammograms of Au electrode. The dissolution rate of oxygen from the open air into the medium is almost equal to the consumptive rate of oxygen by the growth of 1~2 cell/ml of *S. typhimurium* during the first 9 h after adding *S. typhimurium* into the medium. Then, the rapid increased cell numbers consumed oxygen dissolved in the medium rapidly, and at about 10.5 h the dissolved oxygen was used up. The voltammetric peak corresponding to electro-reduction of dissolved oxygen on Au electrode surface disappeared on the cyclic voltammograms (FIG. 2 (curve c)), and the observed current at −0.35 v (vs Ag|AgCl) was only the non-Faradic background current.

The curves of peak currents corresponding to the electro-reduction of dissolved oxygen at −0.35 v (vs Ag|AgCl) as a function of the incubation times for different concentrations of *S. typhimurium* in the medium are shown in FIG. 3. As expected for the medium without *S. typhimurium*, the reduction current of oxygen was constant with time (FIG. 3 (curve a)). Changes in the reduction current of oxygen with incubation times are correlative to the concentrations of *S. typhimurium* inoculated in the medium.

Detection of *S. typhimurium* by Cyclic Voltammetric Method

As the principle of impedance microbiology for rapid detection of microorganisms, the threshold value has to be determined from the growth curve. The incubation time required to reach certain curve features, e.g., the threshold value, is defined as detection time (M. Wawerla, A. Stolle, B. Schalch, H. Eisgeruber, J. Food. Prot. 62 (1999) 1488). In our cyclic voltammetric method for detecting *S. typhimurium*, the measured peak current values at −0.35 v (vs Ag|AgCl) are plotted against the incubation times (FIG. 3). The curves of peak currents as a function of incubation times were termed as oxygen consumption curve corresponding to the impedance curve in impedance microbiology. Threshold value and detection time could be obtained from the corresponding oxygen consumption curve. The graphic presentation of oxygen consumption curve and the threshold value and detection time are illustrated in FIG. 4.

FIG. 5 shows the relationship between *S. typhimurium* cell numbers inoculated in the medium and detection times.

Data points in FIG. 5 represent the mean of three replicate measurements with the standard deviation for each concentration of S. typhimurium. The concentrations of S. typhimurium are the mean of three plating counts. It is indicated in FIG. 5 that the detection times are inversely related to the concentrations of S. typhimurium in the medium. A linear range between the concentrations of S. typhimurium and the detection times could be obtained for bacteria concentrations ranging from $10^0$ to $10^6$ cells/ml. The regression model can be expressed as: $t_D=-1.3N+9.9$, $R^2=0.989$. Where $t_D$ is the detection time in hours; N is the logarithmic value of S. typhimurium cell numbers in CFU/ml. The detection limit was 1~2 cell/ml, and the detection time was 10 h for 1~2 cell/ml in the medium. It only took 2.1 h to get the result for the samples containing $1~2\times10^6$ cells/ml. This method is more sensitive than any of the antibody-based methods and nucleic acid-based polymerase chain reaction (PCR) methods that have been reported. For example, enzyme-linked immunomagnetic electrochemical detection of S. typhimurium could only have a detection limit of $8\times10^3$ cell/ml (A. G. Gehring, C. G. Crawford, R. S. Mazenko, L. Van Houten, J. D. Brewster, J. Immunol. Methods. 195 (1996)15).

Our recently developed methods based on immunomagnetic separation and flow-injection tyrosinase-modified electrode detection could only give a detection level of $5\times10^3$ cells/ml (Y. H. Che, Z. Yang, Y. Li, D. Paul, M. Slavik, J. Rapid. Methods. Automat. Microbiol. 7 (1999) 47). It is almost impossible to detect 1 cell/ml of bacteria without pre-enrichment using immuno-based methods because of the limited capture efficiency of antibodies to bacteria and non-specific binding of reporter antibody. Theoretically, polymerase chain reaction should be very sensitive because small quantities of DNA extracted from bacteria could be amplified to produce large amount of detectable DNA. PCR methods for detection of bacteria could only produce a detectable level ranging from $10^1$ to $10^4$ cells/ml for different food samples depending on the efficiency of DNA extraction, non-specific amplifications and in the presence of inhibitors in various foods (J. L. McKillip, L. A. Jaykus, M. A. Drake, J. Appl. Microbiol. 89 (2000) 49; H. A. Powell, C. M. Gooding, S. D. Garrett, B. M. Lund, R. A. McKee, Lett. Appl. Microbiol. 18 (1994) 59.). The sensitivity of PCR for bacteria is still not comparable with conventional methods. The cyclic voltammetric method developed in this research for detection of S. typhimurium has the sensitivity similar to the conventional culture method and impedimetric method but is much more rapid than these methods.

Figure 6:
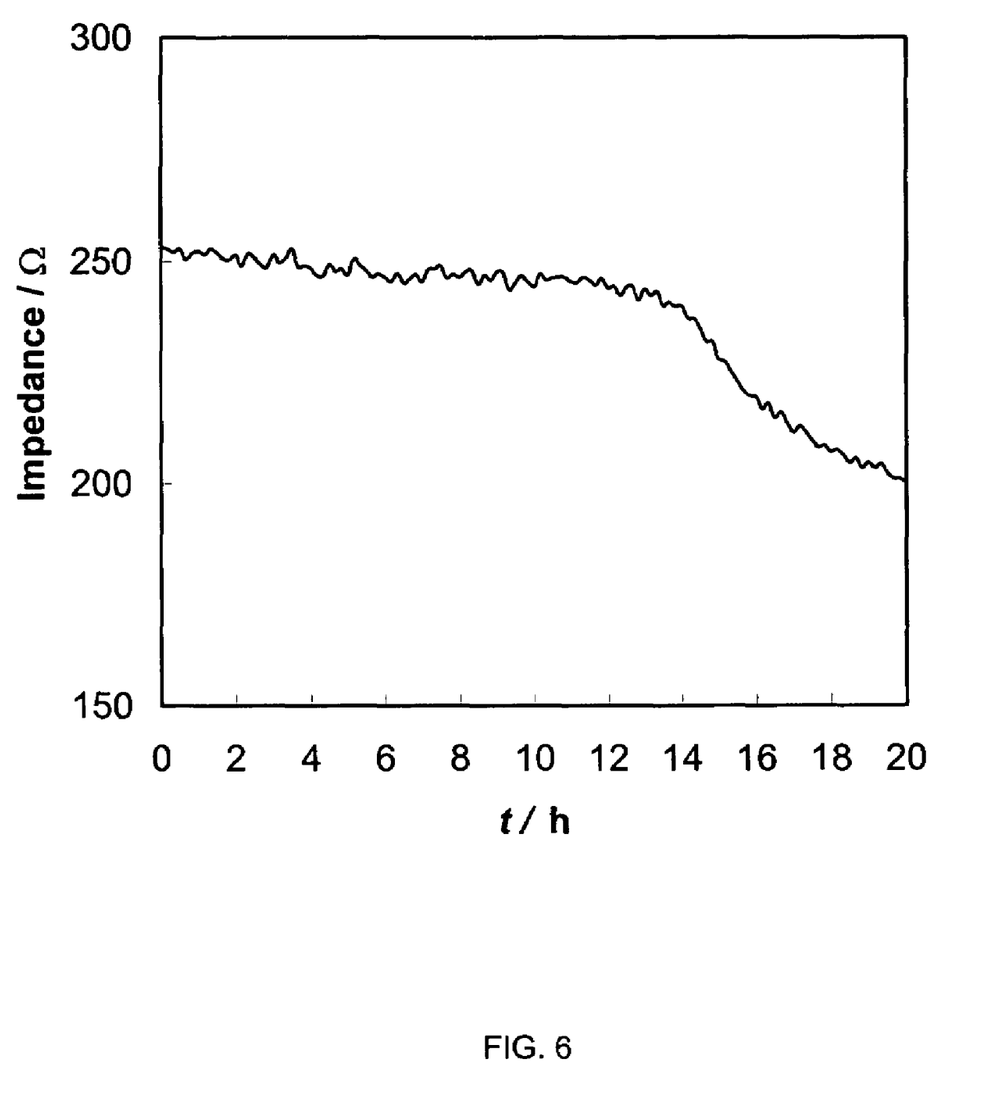
FIG. 6 is a typical impedance curve of S. typhimurium ($1.7\times10^1$ cells/ml) in SCT/M medium.

In applications of this method, food samples, either liquid or solid, can be directly introduced into the detection cell containing selective medium without any pretreatments such as filtration and centrifugation. The impedance method for detection of S. typhimurium was also tested using SCT/M as a selective medium in this research in order to compare the impedimetric method with the cyclic voltammetric method. The impedance curve for $10^1$ cells/ml of S. typhimurium was shown in FIG. 6, the detection time for $10^1$ cells/ml of S. typhimurium is approximately 15 h using such an impedimetric method. Furthermore, impedance microbiology requires special media that have a sensitive response in impedance.

Figure 1:
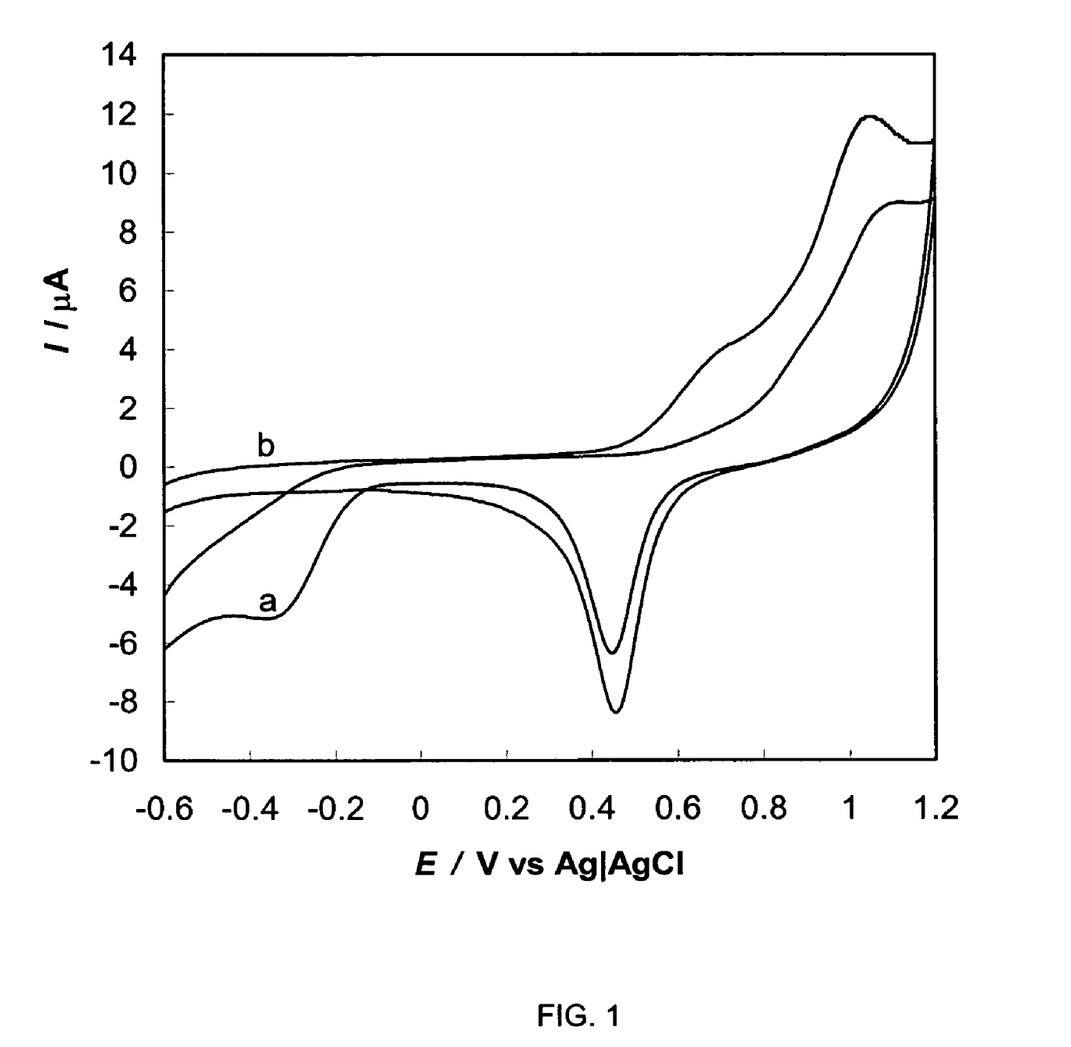
FIG. 1 is a graph of cyclic voltammograms of Au electrode in the oxygen-saturated SC/M medium (a) and deoxygenated SC/M medium (b) at a scan rate of 100 mV/s.
Figure 2:
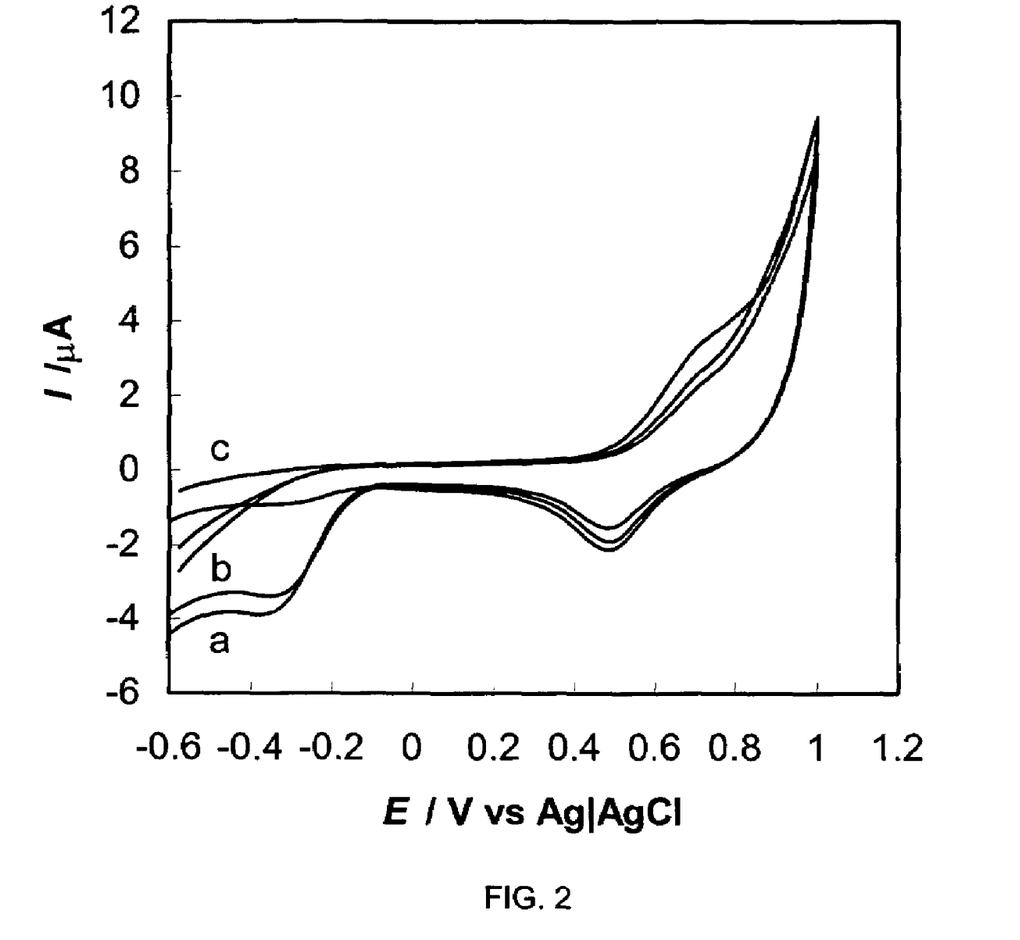
FIG. 2 is a graph of cyclic voltammograms of Au electrode in the SC/M medium at a scan rate of 100 mV/s during the growth of S. typhimurium. (a) at the beginning of adding S. typhimurium ($1~2\times10^0$ cells/ml); (b) after 9 h growing of S. typhimurium; (c) after 10.5 h growth of S. typhimurium.
Figure 3:
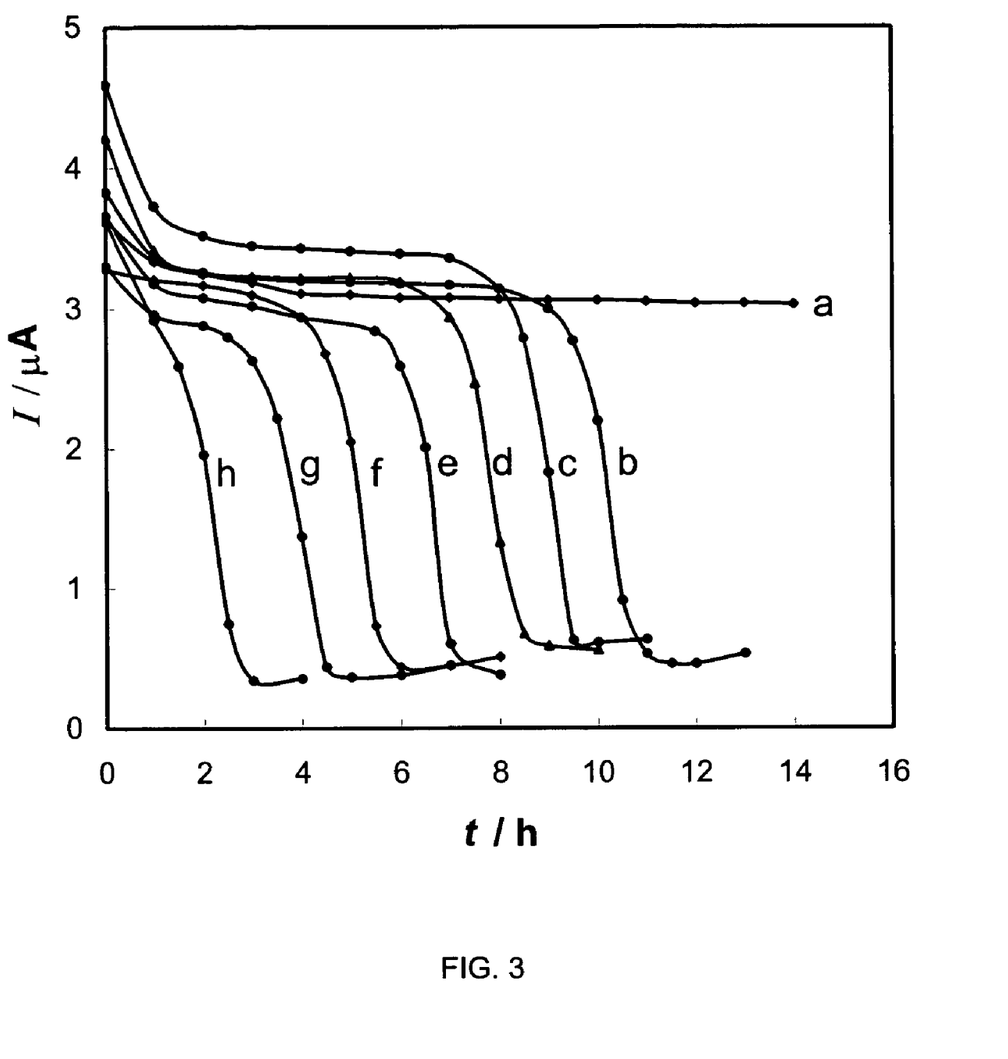
FIG. 3 is a graph showing the curves of peak currents on cyclic voltammograms at $-0.35$ v (vs Ag|AgCl) as a function of the incubation times for different concentrations of S. typhimurium in the medium. (a, b, c, d, e, f, g and h correspond to the concentrations of 0, $10^0$, $10^1$, $10^2$, $10^3$, $10^4$, $10^5$ and $10^6$ CFU/ml S. typhimurium, respectively.)
Figure 4:
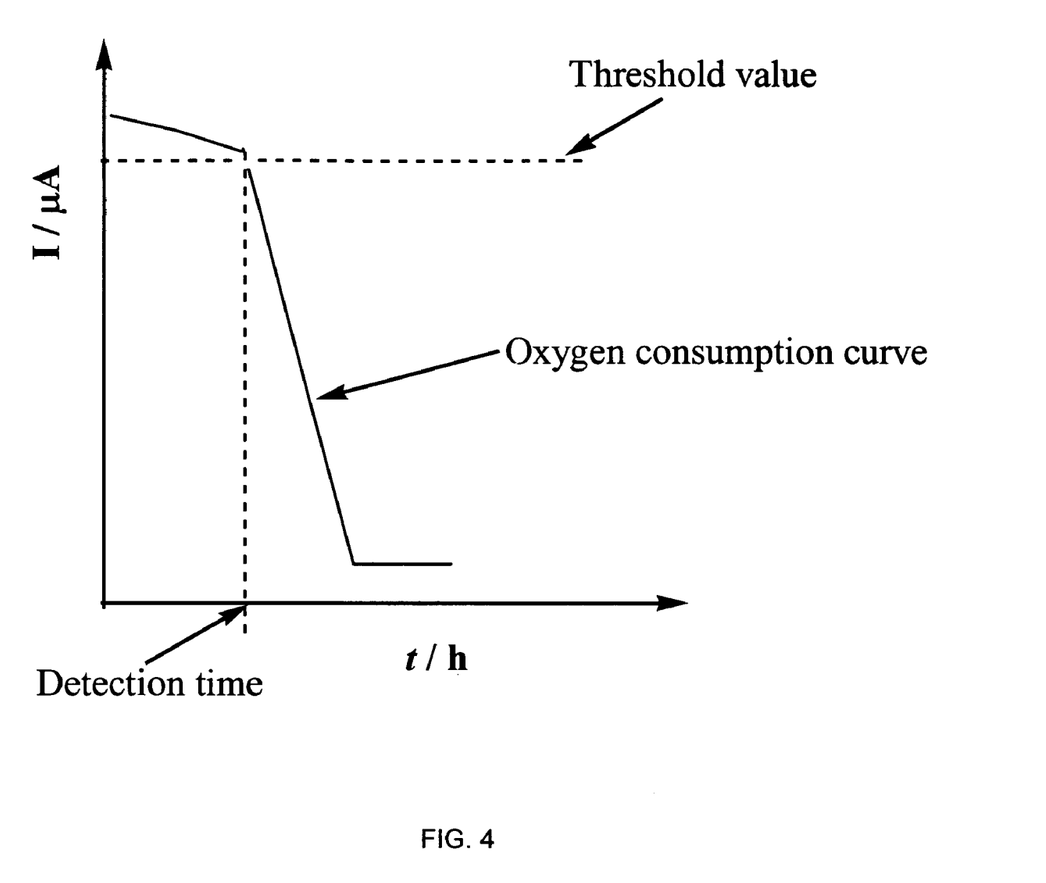
FIG. 4 is a graphic presentation of threshold value and detection time on an oxygen consumption curve.

The reproducibility of the cyclic voltammetric method for detection of S. typhimurium was examined by replicating tests at each concentration of S. typhimurium. The background tests in which there was no S. typhimurium in the medium (FIG. 3 (curve a)) were also replicated 3 times. None of them gave a positive result after recording the cyclic voltammograms for 15 h. The standard deviations from 3 replicates at each concentration are shown in FIG. 5, which indicated that the cyclic voltammetric method is reproducible and has a good correlation with the plate count method.

Escherichia coli O157:H7 and Listeria monocytogenes, two of the major pathogenic bacteria associated with food products, were used as the competing pathogens in examining the specificity of the selective medium for detection of S. typhimurium. The cyclic voltammogram of Au electrode in the SC/M medium containing $1~10\times10^2$ cell/ml of E. coli O157:H7 or L. monocytogenes was automatically recorded at every 10 min for 15 h at 37° C. with a scan potential range from −0.6 v to 1.0 v (vs Ag|AgCl) at a scan rate of 100 mV/s. The reduction peak current of oxygen at −0.35 v (vs Ag|AgCl) did not decrease with time on the cyclic voltammograms. It indicated that these two microorganisms did not grow in the SC/M broth, and would not interfere in the detection of S. typhimurium if present in a sample.

The reduction peak of oxygen dissolved in the SC/M medium on the gold electrode surface at −0.35 v (vs Ag|AgCl) in the cyclic voltammograms at the scanning rate of 100 mV/s and the scan potentials ranging from −0.6 v to +1.0 v could be used for quantitative and qualitative detection of microbial growth. Our results demonstrate that study on the changes in electrochemical and/or optical properties of a medium during the growth of microorganisms may lead to new strategies for rapid detection of pathogens. This research could open a new way for rapid detection of S. typhimurium in various samples such as food, environmental and clinical samples.

EXAMPLES

Example 1—Materials

Salmonella typhimurium (ATCC 14028) as a target pathogen was obtained from Dr Amy Waldroup (Centers of Excellence for Poultry Science, University of Arkansas). Escherichia coli O157:H7 (ATCC 43888) and Listeria monocytogenes (FDA 10143) as competing bacteria were obtained from American Type Culture Collection (Rockville, Md.). Fluid selenite cystine Broth, mannitol, trimethylamine oxide and disodium phosphate were purchased from Sigma-Aldrich (St. Louis, Mo.). Deionized water from Millipore (Milli-Q, 18.2 MΩ/cm) (Millipore, Bedford, Mass.). Buffered peptone water (BPW) was purchased from Remel (Lenexa, Kans.). Gold disk electrodes consisting of a 1.6 mm diameter disk embedded in the end of a 6 mm diameter Kel-F cylinder, platinum auxiliary electrodes, reference electrodes (Ag|AgCl) and polishing materials were from Bioanalytical Systems, Inc. (West Lafayette, Ind.).

Example 2—Apparatus

A BAS CV-50W electrochemical analyzer and IM-6 impedance analyzer (Bioanalytical Systems, Inc., West Lafayette, Ind.) were equipped with a water-jacketed glass vial (15 ml) as an incubator containing three electrodes (Au working electrode, platinum auxiliary electrode and an (Ag|AgCl) reference electrode). The temperature in the incubator was controlled at 37±0.5° C. by a thermostatic bath.

Example 3—Bacteria and Conventional Plating Method

A pure culture of S. typhimurium was grown in 5 ml BPW broth at 37° C. for approximately 17~18 h before use. The culture was serially diluted from 1 to $10^{-8}$ with selenite cystine/mannitol medium (SC/M). SC/M medium was prepared by adding 17 g fluid selenite cystine and 5 g mannitol into 1 L deionized water. SC/M medium was sterilized by boiling. The prepared medium was stored at 2–8° C. Plate counting was performed by plating 0.1 ml of dilutions on xylose lysine tergitol agar (XLT$_4$) (Difco, Detroit, Mich.). After incubation at 37° C. for 24 h, *S. typhimurium* colonies on the plate were counted to determine the number of colony forming units of *S. typhimurium* per ml (CFU/ml) in the culture. A pure culture of *E. coli* or *L. monocytogenes* was grown in 5 ml brain heart infusion (BHI) at 37° C. for approximately 17~18 h before use. The number of *E. coli* or *L. monocytogenes* in pure culture was determined by plate counting methods. Colonies of *L. monocytogenes* were enumerated after incubation at 37° C. for 48 h using Oxoid agar (Oxoid, Basingstoke. Hampshire, UK). Colonies of *E. coli* were enumerated after incubation at 37° C. for 24 h using MacConkey sorbitol agar (remel, Lenexa, Kans.).

Example 4—Electrode and Electrochemical Measurements

A gold electrode was used as a working electrode. The working electrode was first polished with BAS polishing kits, and the polished electrode was sonicated in deionized water for 5 min after each polishing step. Electrochemical measurements were carried out in a conventional three-electrode cell at 37±0.5° C. with a working volume of 15 mL. A platinum wire counter electrode, an Ag|AgCl|NaCl reference electrode and a cleaned gold electrode were introduced into the cell containing 15 ml SC/M medium solution. 15 μl of diluted *S. typhimurium* pure culture was added into the SC/M medium. Cyclic voltammograms were automatically recorded at regular intervals (e.g., every 10 min) at a scan rate of 100 mV/s.

Impedance measurements were performed using IM-6 impedance analyzer linked to a personal computer at a frequency of 1 MHz and an open circuit potential using alternate voltage of 5 mV. The data was recorded at every 10 min for 20 h.

Before each experiment, cells and three electrodes were dipped into 75% ethanol solution for 2 h, and then sterilized for 15 min by boiling in a water bath. Prior to adding the medium into cells, cells and electrodes were sonicated for 10 min in deionized water. The temperature in the cells containing medium was kept for 37±0.5° C. before 15 μl of *S. typhimurium* was inoculated into the medium.

Example 5—Detection of *Listeria monocytogenes*

Figure 7:
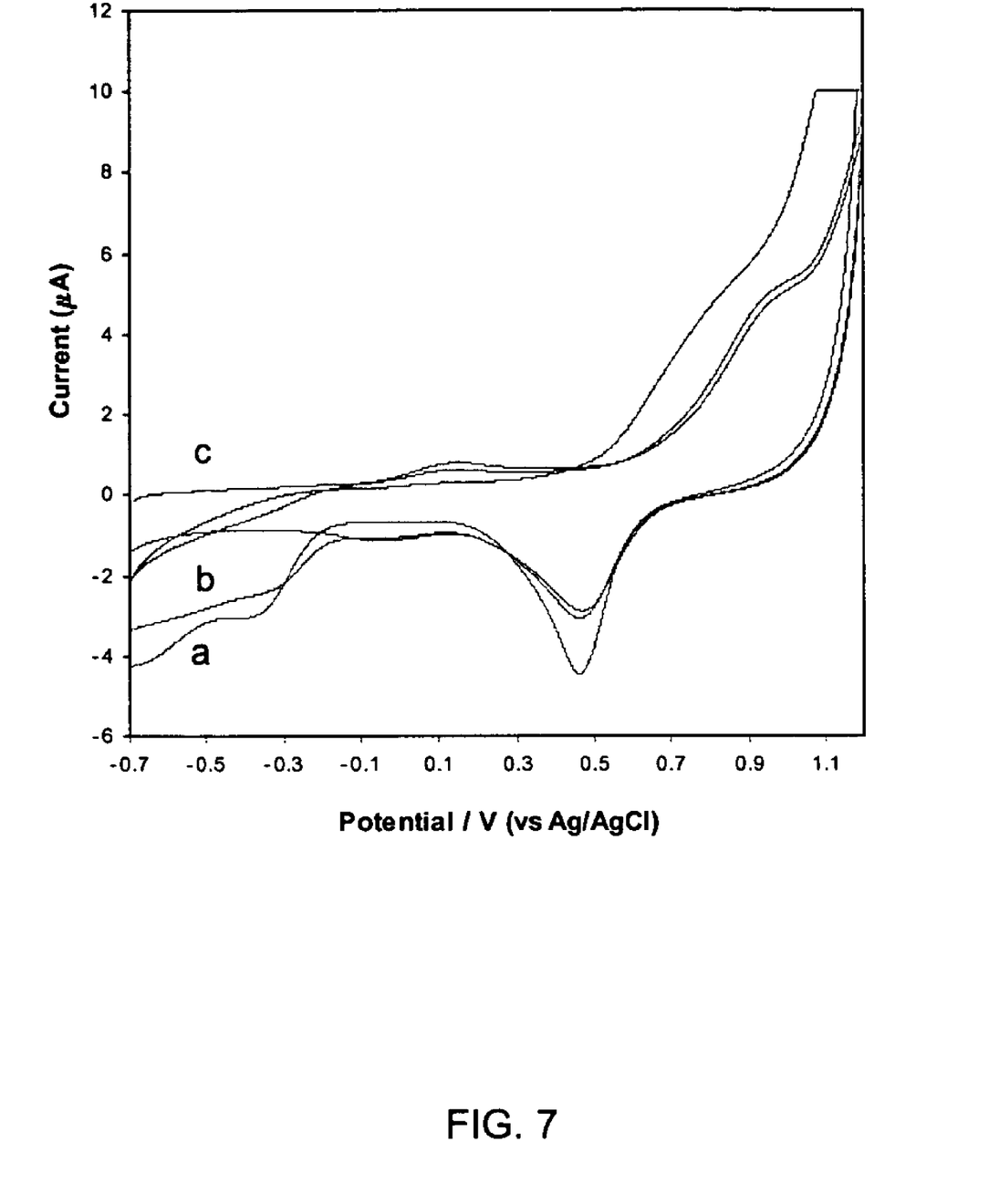
FIG. 7 is a graph of cyclic voltammograms of Au electrode in LEB at a scan rate of 100 mV/s during growth of Listeria monocytogenes. (a) at the beginning of inoculating L. monocytogenes ($2.8\times10^1$ cells/ml); (b) after 13.5 h growing of L. monocytogenes; (c) after 15.5 h growth of L. monocytogenes.
Figure 8:
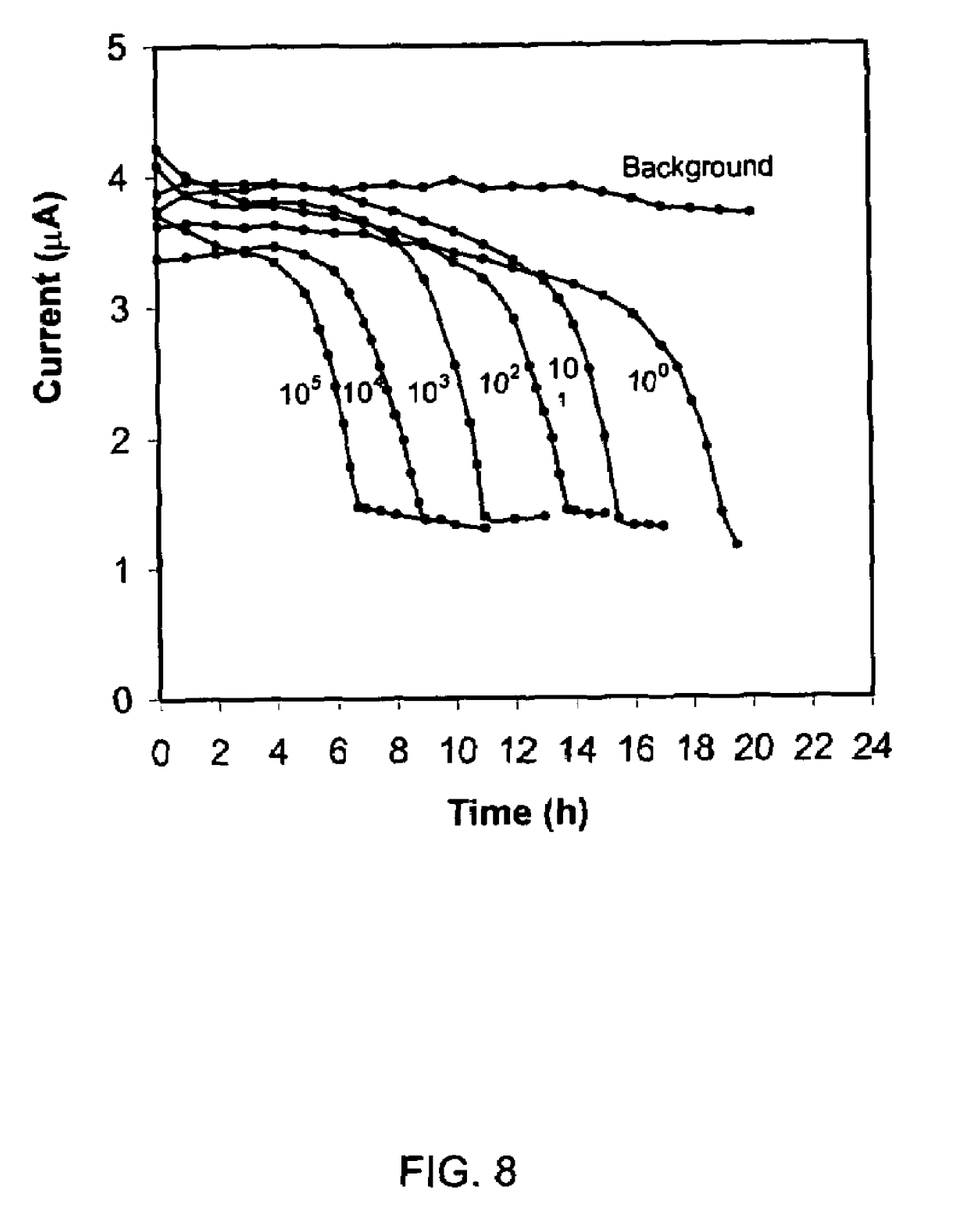
FIG. 8 is a graph showing the curves of peak currents on cyclic voltammograms at $-0.4$ v (vs Ag/AgCl) as a function of the incubation times for different concentrations of L. monocytogenes in the broth. Each curve from right to left corresponds to the concentrations of $10^0$, $10^1$, $10^2$, $10^3$, $10^4$ and $10^5$ CFU/ml of L. monocytogenes, respectively.
Figure 9:
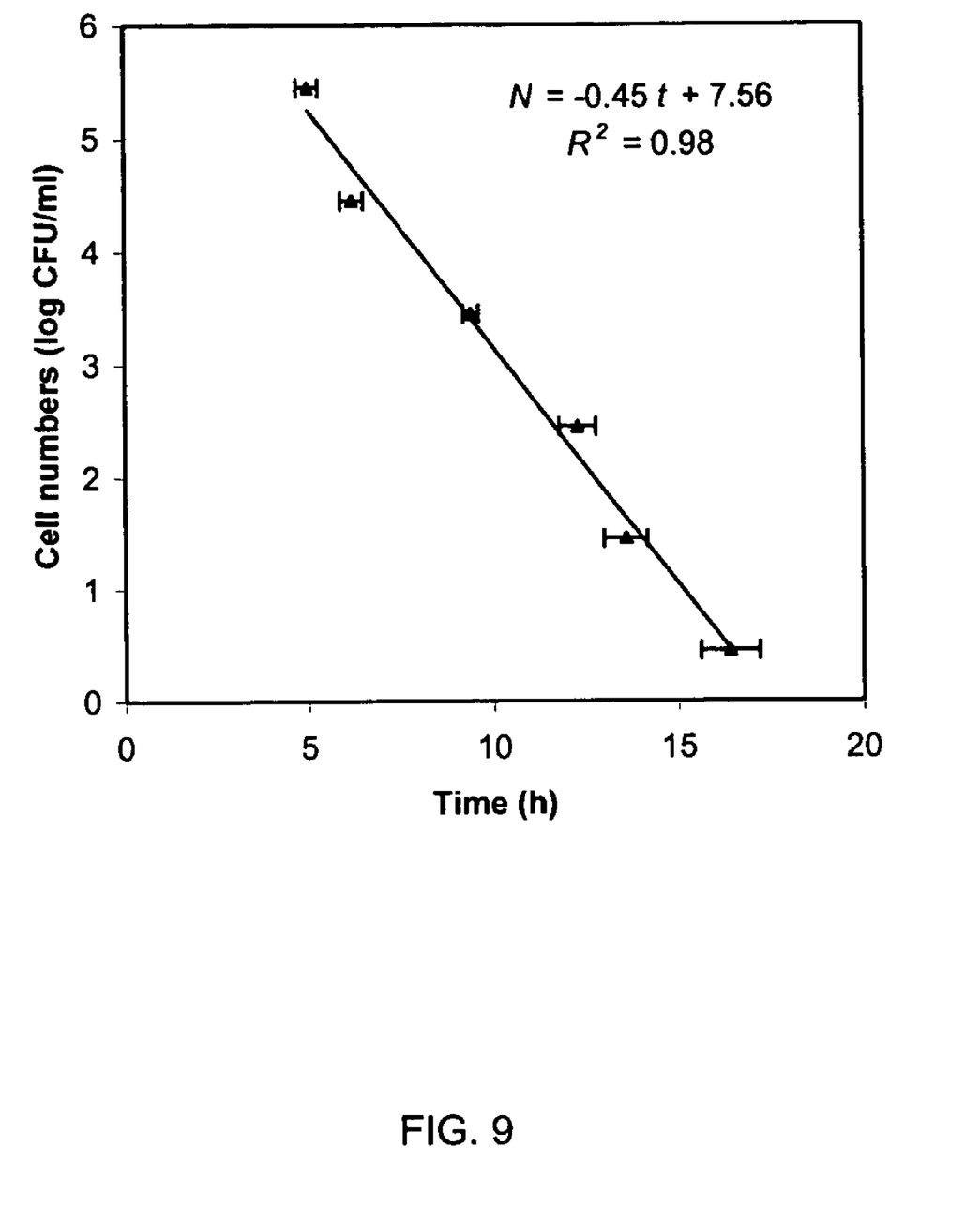
FIG. 9 is the calibration curve for detection of L. monocytogenes using the electrochemical method. Error bars represent the standard deviation of three replicates.

Detection of *Listeria monocytogenes* was also accomplished using cyclic voltammetry. *Listeria* Enrichment broth (LEB) was used as a selective medium for the isolation and enrichment of *L. monocytogenes* in the test. Voltammetric measurement showed that the reduction of oxygen at a gold electrode produced a cathodic peak at –0.4 V (FIG. 7). The peak current at –0.4 V was plotted as a function of the bacterial growth time, producing an oxygen consumption curve of *Listeria monocytogenes* (FIG. 8). A linear relation was found between the detection time (t) obtained from the oxygen consumption curve and the concentration of *L. monocytogenes* in the medium (N) as shown in FIG. 9. The regression equation was N=–0.45 t+7.56 with $R^2$=0.98 in the bacterial concentrations ranging from $10^0$ to $10^5$ CFU/ml. The detection times for $2.8 \times 10^1$ CFU/ml and $10^5$ CFU/ml of *L. monocytogenes* was 15.5 h and 5 h, respectively. The detection limit was 1–2 CFU/ml in the medium. The results of three replicates at each bacteria concentration showed the good reproducibility of this method. The selectivity of this method was evaluated using *S. typhimurium* and *E. coli* O157:H7 as the competing bacteria which had no interference on the detection of *L. monocytogenes*. Milk was used as a food sample to evaluate the cyclic voltammetric method for the detection of *L. monocytogenes*. The results obtained from this method agreed well with those obtained from plate counting method.

Example 6—Detection of *E. coli* O157:H7

Figure 10:
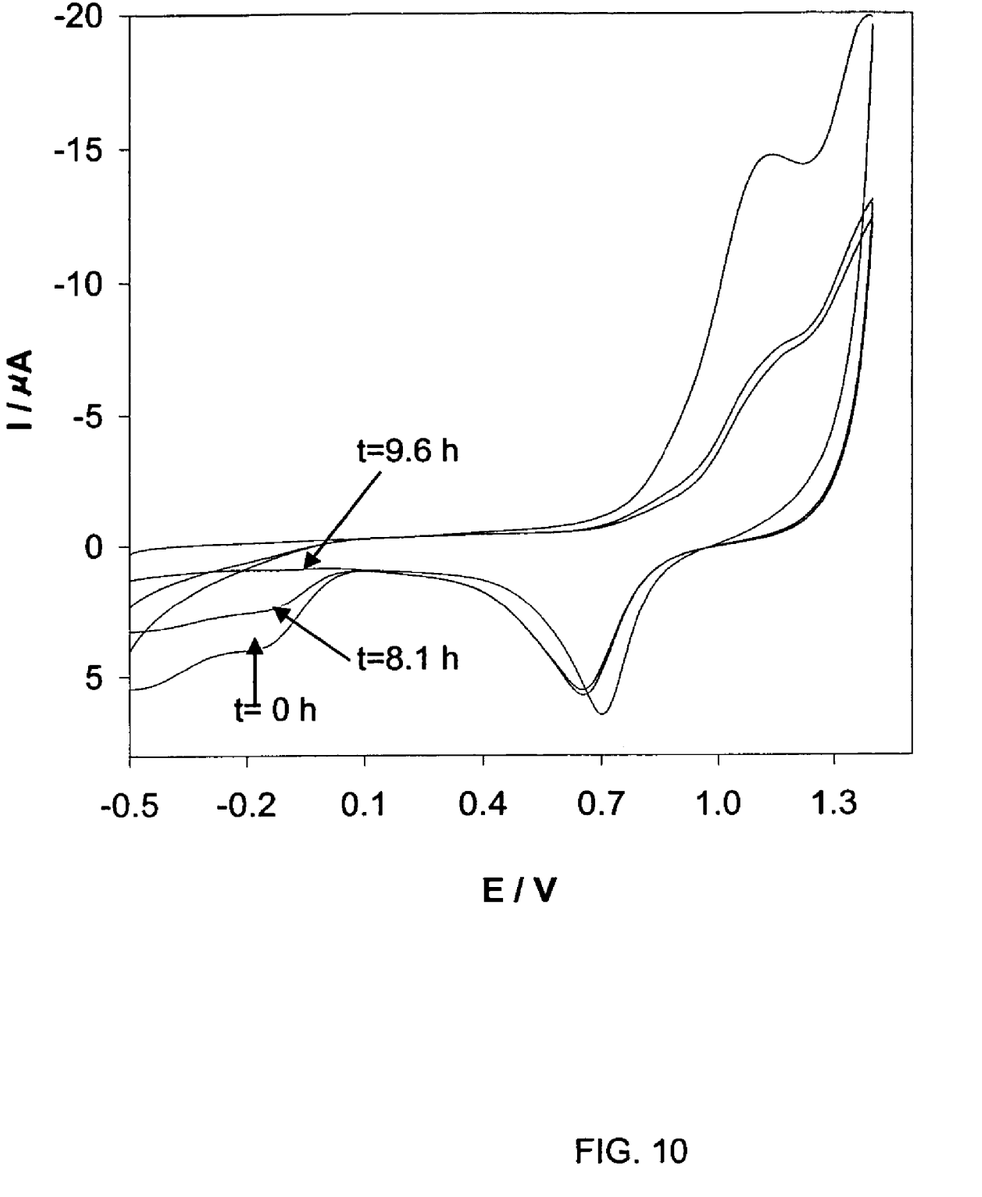
FIG. 10 is a graph of cyclic voltammograms at different growth times during E. coli O157:H7 growth in mEC broth. Peak current at $E=-0.16$ V decreases with growth time.
Figure 11:
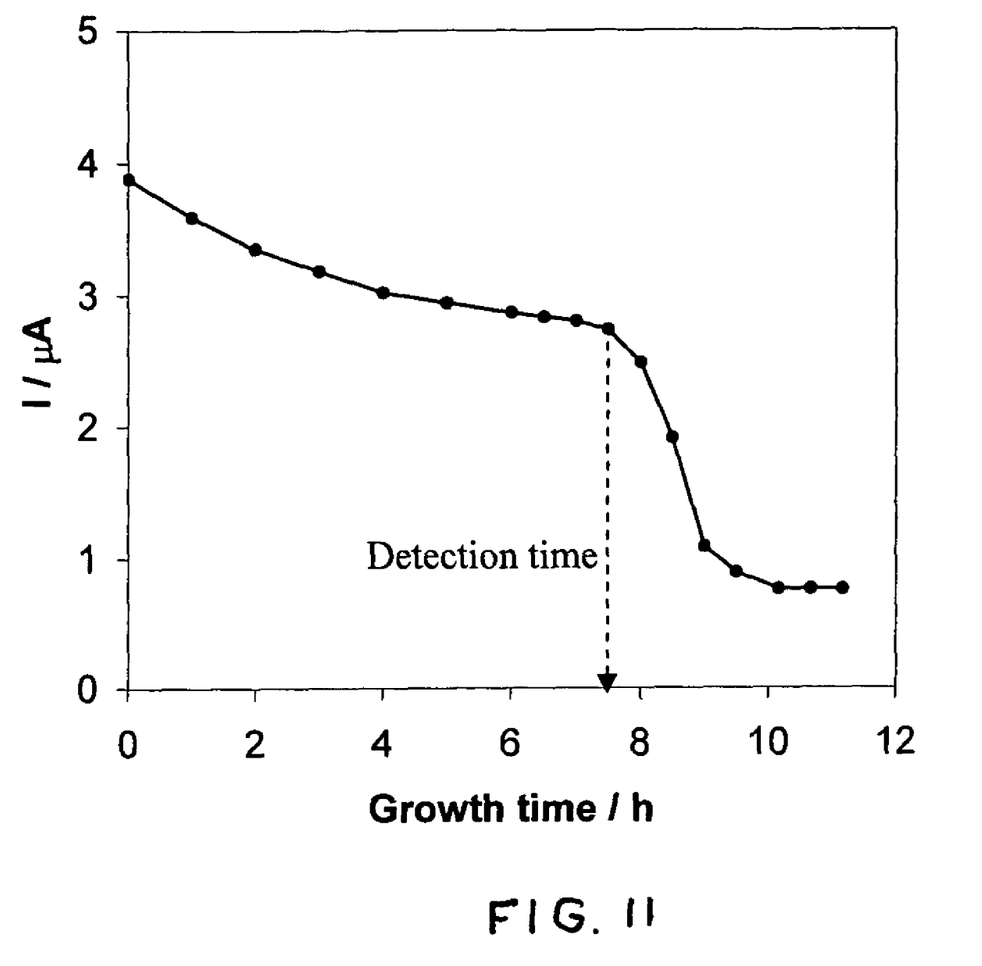
FIG. 11 is a growth curve of E. coli O157:H7 in mEC broth at initial cell number of $4.0\times10^3$ CFU/ml.

*E.coli* O157:H7 was detected using cyclic voltammetry. mEC broth with novobiocin was used as a selective medium for the growth of *E. coli* O157:H7. Voltammetric measurement showed that the reduction of oxygen at a gold electrode produced a cathodic peak at –0.16 V. The peak current at –0.16 V reduced with the increasing growth time, and disappeared completely finally (FIG. 10). This peak current was plotted as a function of the bacterial growth time, producing an oxygen consumption curve of *E. coli* O157:H7 (FIG. 11). Due to the microorganism multiplication, the peak current at –0.16 V started to decease sharply at a point which was defined as the detection time. The detection time for $4.0 \times 10^3$ CFU/ml of *E. coli* O157:H7 was 7.5 h. The detection limit was 1–2 CFU/ml in the medium.

What is claimed is:

1. A method for detecting the concentration of viable pathogenic bacteria in a sample, comprising the steps of:
   a. inoculating a selective culture medium with the sample;
   b. monitoring oxygen consumption during the growth of the pathogenic bacteria in the selective culture medium using cyclic voltammetry to obtain the cathodic peak current;
   c. plotting the cathodic peak current against the pathogenic bacterial growth time to generate an oxygen consumption curve;
   d. observing a detection time on the oxygen consumption curve at which time the decrease in the cathodic peak current exceeds a threshold value; and
   e. calculating the concentration of pathogenic bacteria in the sample by comparison of the detection time to a calibration curve of detection time versus initial cell concentration.

2. The method of claim 1, wherein the cyclic voltammetry is by a three electrode system in which the working electrode is a gold electrode.

3. The method of claim 1, wherein the pathogenic bacteria is *Salmonella typhimurium*.

4. The method of claim 3, wherein the selective culture medium is selenite cystine/mannitol.

5. The method of claim 1, wherein the pathogenic bacteria is *Listeria monocytogenes*.

6. The method of claim 5, wherein the selective culture medium is *Listeria* Enrichment Broth.

7. The method of claim 1, wherein the pathogenic bacteria is *Escherichia coli* O157:H7.

8. The method of claim 7, wherein the selective culture medium is mEC broth with novobiocin.

9. A method for detecting the concentration of viable bacteria in a sample, comprising the steps of:
   a. monitoring oxygen consumption during the growth of the bacteria in the selective culture medium using cyclic voltammetry to obtain the cathodic peak current;
   b. plotting the cathodic peak current against the bacterial growth time to generate an oxygen consumption curve; and
   c. observing a detection time on the oxygen consumption curve at which time the decrease in the cathodic peak current exceeds a threshold value.

* * * * *